US00PP30670P2

(12) United States Plant Patent
Horvath

(10) Patent No.: US PP30,670 P2
(45) Date of Patent: Jul. 9, 2019

(54) ***GEUM* PLANT NAMED 'TOP SHELF MARGARITA'**

(50) Latin Name: ***Geum* hybrid**
Varietal Denomination: Top Shelf Margarita

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 15/732,681

(22) Filed: Dec. 14, 2017

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new, distinct *Geum* plant as illustrated and described, characterized by single wavy yellow flowers on purple stems.

1 Drawing Sheet

Latin name: *Geum* hybrid.
Cultivar name: 'Top Shelf Margarita'.

BACKGROUND OF THE INVENTION

The present invention relates to a new and distinct hybrid of *Geum* plant named 'Top Shelf Margarita' characterized by single, wavy yellow flowers on up to 33 cm purple stems. The new *Geum* was discovered and developed as a seedling as part of an ongoing breeding and selecting program in Hebron, Ill. in 2010. The plant was raised from seed on open pollinated plants. The parents of the new plant are unknown. The selection of the new plant was made in 2014 and was due to its' single, wavy yellow flowers on up to 33 cm purple stems. The initial asexual propagation of the new *Geum* plant was by division and took place at a nursery in Hebron, Ill. since 2015. Continued asexual propagation by division since that time has shown that the unique features of the new *Geum* plant are stable and reproduced true to type in successive generations. No plants of the new *Geum* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

In the following description, color references are made to The Royal Horticultural Society Colour Chart (2001). The new *Geum* plant named 'Top Shelf Margarita' characterized by single, wavy yellow flowers 7 B on purple stems have been observed to be unique and stable. The parent plants are no longer available for comparison.

Plants of the new *Geum* can be compared to *Geum* 'Banana Daiquiri' U.S. Plant Pat. No. 25,351, patented. 1. The new plant flower color is 7 B while *Geum* 'Banana Daiquiri' has semi-double flowers colored of RHS 3 B. 2. The size of *Geum* 'Banana Daiquiri' plants are 36 cm while the new *Geum* plant reaches 33 cm.

Plants of the new *Geum* can also be compared to *Geum* 'Gimlet' U.S. Plant Pat. No. 26,223, patented. 1. The new plant flower color is 7 B while *Geum* 'Gimlet' has a flower color of 4 A. 2. The size of *Geum* 'Gimlet' plants are 40 cm while the new *Geum* plant reaches 33 cm.

DESCRIPTION OF PHOTOGRAPHS

Figure 1:
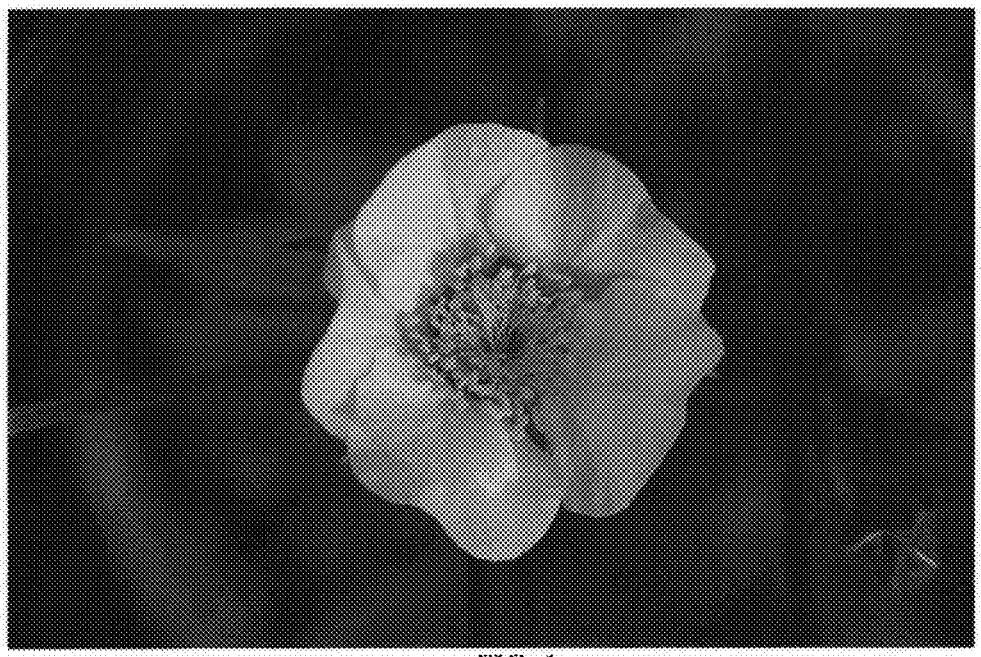
Figure 2:
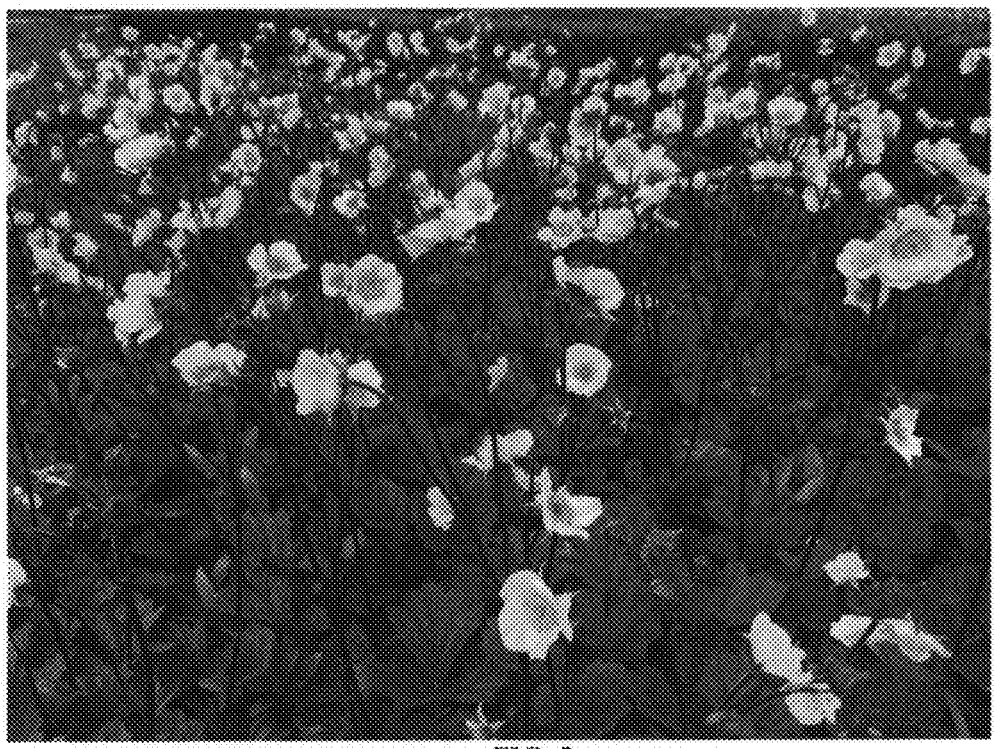

FIG. 1. Close up of the flower.
FIG. 2. Blooming plants in May.

DETAILED BOTANICAL DESCRIPTION

In the following description, color references are made to The Royal Horticultural Society Colour Chart (2001). Plants used for the description were grown in a 1 gallon container for one year at a nursery in Hebron, Ill. Measurements and numerical values represent averages of typical plants.

Botanical classification: *Geum* hybrid cultivar 'Top Shelf Margarita'.

Parentage: Unknown.

Propagation: Vegetative division.

Plant description: Overall habit of the new *Geum* is basal clumps, with upright flower stems colored purple, topped by single wavy flowers of yellow 7 B.

*Plant height.*—33 cm.

*Plant width.*—30 cm.

*Stem.*—Diameter: 3 mm.

*Stem or basal branches.*—Length up to 33 cm, with the internode between basal foliage and first leaflet length being 2 cm and the second internode between the first leaflet and the second leaflet length being 2 cm, the third internode between the second and third leaflet length being 8 cm, the fourth internode between the third and fourth leaflet length being 6 cm.

*Stem coloration.*—Mostly purple N186 C blending into some green 146 D at the tip.

Foliage description:

*Type.*—Herbaceaous.

*Arrangement.*—Basal alternate with typically three or four lateral leaflets per stem.

*Petiole*.—Up to 10 cm long, with a diameter of 2 mm, color is mostly purple N186 C blending into some green 146 D at the tip.

*Terminal compound leaf length*.—Up to 32 mm.

*Terminal compound leaf width*.—25 mm.

*Terminal leaflet length*.—Typically 8 mm.

*Terminal leaflet width*.—Typically 12 mm.

*Terminal leaflet shape*.—Obovate with incised margins.

*Terminal and lateral leaf apex*.—Acute.

*Terminal and lateral leaf base*.—Cuneate.

*Terminal and lateral leaf margin*.—Incised.

*Texture*.—Terminal and lateral leaf, upper and lower surfaces: pubescent.

*Venation pattern*.—Terminal and lateral leaf, upper and lower surfaces: pinnate.

*Venation color*.—Terminal and lateral leaf, upper surface is color 145 A and lower surface color is 145 C.

*Lateral leaflet number*.—3 or 4 per stem.

*Lateral leaflet length*.—21 mm.

*Lateral leaflet width*.—Up to 11 mm.

*Lateral leaflet shape*.—Obovate.

*Terminal and lateral adaxial leaf color description*.—146 A.

*Terminal and lateral abaxial leaf color description*.—146 C.

Flower description:

*Flower type*.—Corymb.

*Adaxial flower color*.—7 B. Abaxial Flower color — 8 A.

*Flower size*.—Diameter: 40 mm across, depth 15 mm.

*Flower number*.—3 per stem, 25 per plant. Average Number Flowering Stems — 8.

*Bloom period and duration*.—Beginning the last week of April into the last week of May in Hebron, Ill.

*Flower longevity and duration on the plant*.—Approximately 2-3 weeks.

*Flower longevity and duration cut*.—Approximately 5 days.

*Scent*.—None.

*Petal count*.—Up to 9. Petal shape — spathulate.

*Petal arrangement*.—Rotate, overlapping.

*Petal diameter or width*.—19 mm across and petal length — 15 mm long.

*Petal apex*.—Retuse and lobulate, base: attenuate, margin: entire and sinuate.

*Petal texture*.—Upper and lower surfaces: smooth, glabrous.

*Petal color*.—Upper surface is 7 B. Petal color — lower surface color is 8 A.

*Petal venation*.—Type — reniform, vein color — upper surface 7 B, lower surface 8 A.

*Inflorescence diameter and height*.—11 cm across, 12 cm long.

*Flower buds*.—Diameter: 10 mm across, depth: 15 mm, shape: ovoid, surface: slightly pubescent and color 187 B.

*Sepal size*.—Length: up to 12 mm, diameter: 8 mm at base coming to a point.

*Sepal quantity*.—6.

*Sepal shape*.—Lanceolate, apex: acute, base: cuneate, margin: entire.

*Sepal texture*.—Upper and lower surfaces: Pubescent.

*Sepal color*.—Adaxial color 146 C. Abaxial color N186 C.

*Peduncle color*.—N186 C.

*Peduncle size*.—Length: 12 mm, diameter: 2 mm.

*Pedicel size*.—Length: 11 cm, diameter: 2-3 mm and color N186 C.

*Reproductive organs*.—Stamen — quantity 100-200, length 3 cm. Color 3 B.

*Anther*.—Quantity: 150, length: 1 mm, diameter: close to 0.5 mm.

*Pollen*.—Color: 17 B.

*Stigma*.—Number 75, Length 2 mm, width less than 1 mm, color is close to 15 A.

*Style*.—Number: 75, length: 9 mm. Pistil — number: 75, length: 1-2 mm. color is close to 15 A, green 146 C at the base.

*Pistil*.—Number: 75, length 11 mm.

*Ovaries*.—Number: 75, color is 146 C.

*Fruit*.—Number: 75, a cluster of tear shaped achenes 9-10 mm long and 2 mm wide with 1-2 mm styles. Color — brown.

*Hardiness*.—USDA zone 4-8.

Disease resistance: Resistance to diseases common to *Geum* has not been observed on plants grown under nursery conditions.

I claim:

1. A new, distinct *Geum* plant as illustrated and described, characterized by single wavy yellow flowers on purple stems.

* * * * *